(12) United States Patent
Ausserre et al.

(10) Patent No.: US 7,209,232 B2
(45) Date of Patent: Apr. 24, 2007

(54) DEVICE FOR ELLIPSOMETRIC TWO-DIMENSIONAL DISPLAY OF A SAMPLE, DISPLAY METHOD AND ELLIPSOMETRIC MEASUREMENT METHOD WITH SPATIAL RESOLUTION

(75) Inventors: Dominique Ausserre, Soulitre (FR); Marie-Pierre Valignat, Boulogne (FR)

(73) Assignees: Centre National de la Recherche Scientifique (CNRS), Paris (FR); Universite Pierre et Marie Curie, Paris (FR)

( * ) Notice: Subject to any disclaimer, the term of this patent is extended or adjusted under 35 U.S.C. 154(b) by 477 days.

(21) Appl. No.: 10/450,958

(22) PCT Filed: Dec. 18, 2001

(86) PCT No.: PCT/FR01/04046

§ 371 (c)(1),
(2), (4) Date: Dec. 23, 2003

(87) PCT Pub. No.: WO02/50513

PCT Pub. Date: Jun. 27, 2002

(65) Prior Publication Data

US 2004/0085537 A1    May 6, 2004

(30) Foreign Application Priority Data

Dec. 18, 2000   (FR) .................................. 00 16529

(51) Int. Cl.
*G01J 4/00* (2006.01)
(52) U.S. Cl. ...................................... 356/369; 250/225
(58) Field of Classification Search ................ 356/364, 356/369; 250/225, 559.09
See application file for complete search history.

(56) References Cited

U.S. PATENT DOCUMENTS 5,333,052 A * 7/1994 Finarov ...................... 356/369

(Continued)

FOREIGN PATENT DOCUMENTS

DE          43 11 726          1/1995

(Continued)

OTHER PUBLICATIONS

Jin G et al:, "Imaging Ellipsometry for the Visualization of Bio-Molecular Layers" Engineering in Medicine and Biology Society, 1998. Proceedings of the 20th Annual International Conference of the IEEE Hong Kong, China Oct. 29-Nov. 1, 1998, Piscataway, NJ, USA IEEE, Oct. 29, 1998, pp. 581-584, XP001035145 ISBN: 0-7803-5164-9 p. 581, colonne de droite, derniere ligne-p. 582, colonne de droite, ligne 2.

(Continued)

*Primary Examiner*—Gregory J. Toatley, Jr.
*Assistant Examiner*—Roy M. Punnoose
(74) *Attorney, Agent, or Firm*—Young & Thompson (57) ABSTRACT

A device for ellipsometric two-dimensional display of a sample placed in an incident medium, observed between an analyser and a polarizer intersected by convergent light reflection, wherein the ellipsometric parameters of the assembly formed by the sample and a substrate whereon it is placed, are used. The substrate comprises a support and a stack of base layers and its ellipsometric properties are known. The ellipsometric properties of the substrate are such that variations of the sample ellipsometric parameters are displayed with contrast higher that the contrast produced in the absence of the substrate. The invention also concerns a display method and an ellipsometric measurement method with spatial resolution.

28 Claims, 4 Drawing Sheets

U.S. PATENT DOCUMENTS 5,450,201 A * 9/1995 Katzir et al. .......... 356/369

FOREIGN PATENT DOCUMENTS

| DE | 197 08 036 | 9/1998 |
|----|------------|--------|
| WO | WO 97 44633 | 11/1997 |

OTHER PUBLICATIONS

Shatalin S V et al:, "Polarisation Contrast Imaging of Thin Films in Scanning Microscopy" Optics Communications, North-Holland Publishing Co. Amsterdam, NL, vol. 116, No. 4/6, May 1, 1995, pp. 291-299, XP000498326 ISSN: 0030-4018 p. 296, colonne de gauche, ligne 3 -colonne de droite, ligne 3.

Dicke J et al:, "Ellipsomicroscopy for Surface Imaging: Contrast Mechanism, Enhancement, and Application to Co Oxidation on PT (110)", Journal of Optical Society of America A (Optics, Image Science and Vision), Jan. 2000, Opt. Soc America, USA, vol. 17, No. 1, pp. 135-141, XP002182387 ISSN: 0740-3232 p. 136, colonne de gauche, dernier alinear -p. 137, colonne de droite, alinea 1.

Patent Abstracts of Japan, vol. 1996, No. 02, Feb. 29, 1996 & JP 07 261092 A (Hamamatsu Photonics KK), Oct. 13, 1995 abrege.

R.M.A. Azzam, N.M.Bashara: "Ellipsometry and Polarized Light" 1987, North-Holland, Amsterdam XP002195238 ISBN: 0-444-87016-4 (paperback) cite dans la demande p. 174, ligne 1-derniere ligne, p. 260, alinea 3 -p. 262, alinea 2 p. 265, dernier alinea—p. 268, dernier alinea p. 357, alinea 1—alinea 2.

* cited by examiner

DEVICE FOR ELLIPSOMETRIC TWO-DIMENSIONAL DISPLAY OF A SAMPLE, DISPLAY METHOD AND ELLIPSOMETRIC MEASUREMENT METHOD WITH SPATIAL RESOLUTION

FIELD OF THE INVENTION

This invention concerns a device for ellipsometric two-dimensional display of a sample, a display method and an ellipsometric measurement method with spatial resolution. It is particularly well suited to display with ellipsometric contrast or interferential contrast.

BACKGROUND OF THE INVENTION

A sample receiving light and reflecting the same will generally modify the polarisation thereof.

It is possible to use this property to visualise a sample or to characterise said sample by measuring its ellipsometric parameters designated generally as ψ and Δ.

In this view, one may, for instance, refer to the book by Azzam and Bashara published in 1979.

Initially, it has been sought to process the extinction of the Fresnel coefficient $r_p$ at the Brewster angle in order to provide an accurate ellipsometric measurement of the parameters ψ and Δ (ellipsometry) or sensitive display of very thin films, notably at the surface of water (Brewster angle microscopy).

Besides, it has been sought to irradiate a zone of a sample under a single incidence and a single azimuth in order to measure the parameters ψ and Δ corresponding to this zone.

The aim within the framework of this invention is to provide simultaneous processing of the parameters ψ and Δ for a number of points of a sample, each defined by their coordinates x and y. This is called ellipsometric two-dimensional display or measurement of a sample.

Moreover, this invention relates to small samples that may be observed, displayed or measured under an optical reflection microscope. It may be conventional microscopy, microscopy with differential interferential contrast or fluorescence microscopy.

This type of microscopic observations poses particular constraints inasmuch as, on the one hand, the microscope lenses have a wide digital aperture which creates observation conditions significantly different from the usual conditions of the ellipsometric measurements wherein the beams, illuminating beams as well as measuring beams (or reflected beams) are generally small aperture collimated beams and, on the other hand, where the illuminating beams are most often distributed uniformly around the normal incidence, i.e. within a range of angles of incidence hardly lending themselves to ellipsometry.

Still, display methods based on the use of an antiglare substrate have been suggested previously, but they resort to the "incoherent reflectivity" of the substrate. The substrates suggested previously are therefore antiglare for a non-polarised light or for a polarised light with a constant polarisation direction relative to the plane of incidence, which is incompatible with the use of a microscope. The principle is based on the minimisation of the second member of the equation (E4).

$$\Phi_N = (\theta, NP) = \frac{1}{2}(|r_p|^2 + |r_s|^2) \qquad E4$$

where $r_p$ and $r_s$ are the complex reflection coefficients of each polarisation on the substrate affected which depend implicitly on x and on y, $\Phi_N(\theta,NP)$ being the normalised flux reflected for an angle of incidence θ, in non-polarised light.

It is obvious that complete extinction is only possible for $|r_p|=|r_s|=0$, which is an extremely restricting condition, since the values of both Fresnel coefficients are set. The condition of complete extinction, $|r_p+r_s|=0$, is far more flexible since it is solely translated into a relation between both Fresnel coefficients, $$r_p = -r_s \qquad E6$$

Antiglare substrates for a polarised light have also been suggested in order to enhance the performances of the ellipsometers, but the ellipsometry and the optical microscopy had been considered until now as incompatible.

The aim of the invention is therefore to provide an ellipsometric two-dimensional display of an object with very small thickness, invisible under optical microscope under observation conditions known as compatible with the use of a commercially available optical microscope.

In spite of this, according to the invention, it is possible simultaneously to visualise the object and to measure its thickness and its index under microscope.

SUMMARY OF THE INVENTION

To this end, the studied object is deposited on a particular substrate, the association of the studied object and of the substrate forming the set under scrutiny that we call—the sample—. The substrate is designed so that the studied object, albeit very thin, suffices by its presence to modify the aspect of the substrate, thereby leading to the display of the object.

In this view, the substrate consists of a base covered with a stack of layers so that, on the one hand, the thickness e of the last layer verifies the condition $d^2/de^2[Ln|r_p+r_s|]=0$ and so that, on the other hand, the minimum of the quantity $|r_p+r_s|$ on the set of values of e is as small as possible.

Similarly, the presence of the object suffices under these conditions to modify, in a way measurable under optical microscope, the parameters ψ and Δ of the substrate, so that the optical characteristics of the object may be extracted from the measured parameters ψ and Δ of the sample.

Thus, the substrate is designed so that the sensitivity of the parameters ψ and Δ of the sample for a small disturbance of its constitutive parameters is very large for small incidence angles, therefore very different from the Brewster angle, while the display and measuring methods suggested are designed, moreover, so that the radial geometry of the microscope has become compatible with the processing of these ellipsometric features.

In a preferred embodiment, implementing a differential interferential microscope (DIC) (thanks to a device inserted in the vicinity of the rear focal plane of the lens, for example a Nomarski device or a Smith device), the illuminating beam, linearly polarised according to the azimuth φ=0, is splitted by the DIC device into two linearly polarised beam according to the directions φ=45° and φ=−45° and offset laterally, relative to one another by a small quantity Δd, both wave planes associated with both these polarisations under-going upon reflection on the sample, phase variations due to the presence or the lack of homogeneity of the object, whereas these phase variations are converted into colour or intensity variations after going, upon the return of the reflected beam, into the DIC device, then in the analyser cross-connected with the polarizer. In this mode of observation, the contrast of the object is optimised thanks to the adjustment of a compensator included in the DIC device. This adjustment consists in switching off the interference between both beams reflected by the non-interesting regions of the sample while adjusting their phase-shift at the device where they produce interference, i.e. at the analyser, whereas the quality of this extinction conditions the quality of the display. The mathematic condition of this extinction is the same as previously, i.e. $r_p+r_s=0$. The condition of maximum sensitivity on the thickness e of the last layer of the stack in this mode of observation is $d^2/de^2[Ln|r_p+r_s|]=0$.

The display method suggested is therefore globally optimal for all the observations under microscope between cross-connected polarizer and analyser, even when a DIC device is included in the microscope.

The invention relates therefore to a device for ellipsometric two-dimensional display of a sample, comprising an object, placed in an incident medium, observed between a convergent light cross-reflected analyser and polarizer, wherein the ellipsometric parameters of the set composed of the object and a substrate whereon it is placed, are processed.

According to the invention:
the substrate comprises a base and a stack of layers and its ellipsometric properties are known,
the ellipsometric properties of the substrate being such that the variations of the ellipsometric parameters of the sample due to the object are displayed with a contrast greater than the contrast produced in the absence of such substrate.

This invention also relates to the features which will appear clearly in the following specifications and which will be considered individually or according to all their technically possible combinations:
the sample is irradiated through a wide-aperture lens such as a microscope lens,
the microscope is a microscope with differential interferential contrast,
the microscope is a fluorescence microscope, This embodiment is most efficient for the display or the detection of objects with nanometric dimensions. The purpose is then to display without solving. It enables in particular to visualise all the individual wire-shaped objects, i.e. distant by a quantity greater than the lateral resolution of the microscope, whereof the length is greater than a micron (polymers, microtubules, collagen, bacteria, DNA, RNA, carbon nanotubes, nanowires, etc.).

the thickness e of the stack layer in contact with the object is such that the complex reflection coefficients $r_p$ and $r_s$ of the substrate verify the condition $d^2/de^2[Ln|r_p+r_s|]=0$,
the optical properties of the substrate are such that the minimum value taken by the quantity $|r_p+r_s|$ over the set of values of e is as small as possible,
the device comprises a polychromatic light source,
the device comprises a monochromatic light source,
the base is in silicon,
More generally speaking, the base is advantageously an absorbing medium, a metal or a semi-conductor whereof the real part of the optical index is greater than 3.3,
the stack consists of a single layer, This layer is advantageously mineral, composed of a mixture $SiO/SiO_2$ in suited proportions.
the layer is a silica layer,
the thickness of the silica layer is of the order of 1025 Å, the incident medium being simply air,
the layer is a magnesium fluoride layer,
the thickness of the layer of $MgF_2$ is of the order of 1055 Å, the incident medium being simply air,
the layer is a polymer layer,
the layer is a polymer layer, with an optical index substantially equal to 1.343, the incident medium being simply air,
the layer is a mineral layer, with an optical index substantially equal to 1.74, the incident medium being simply water,
the layer is a mineral layer, with an optical index substantially equal to 1.945, the incident medium being simply oil with an optical index 1.5,
the layer is discontinuous and composed of silica blocks and with an index of 1.343, of the same height delineating the thickness of the layer and with cross-sectional dimensions significantly smaller than a micrometer, the incident medium being simply air,
the layer is a mesoporous or nanoporous mineral or organic layer with an index substantially equal to 1.343, the incident medium being simply air,
the layer is a mineral aerogel with an index substantially equal to 1.343, the incident medium being simply air,
the device comprises a microscope comprising an aperture diaphragm in the form of a longitudinal slot adjustable around the axis of the microscope enabling to restrict the illuminating cone to a single incidence plane in a selected direction,
the device comprises a microscope comprising an aperture diaphragm in the form of a ring limiting the illuminating cone of the sample around an angle of incidence,
the object is a thin film and the stack comprises a bevelled layer whereof the thickness varies in a monotonic fashion in a direction X along the surface.

This method and this display device are compatible and may be advantageously superimposed to any optical scanning microscopy, to any invisible light optical technique (UV or IR), to any spectroscopy technique, to any non-linear optical technique, to any diffusion or diffraction technique, and to all their combinations. They are in particular compatible with the fluorescence technique, the micro-Raman technique, the confocal microscopy technique, the two-photon microscopy technique and to all their combinations.

The implementation of the present invention with fluorescence microscopy is particularly advantageous. Indeed, the polarisation of the light emitted by a fluorescent sample is often different from the polarisation of the incident beam. The fluorescent marker therefore causes depolarisation of the light at which the device of the invention is particularly sensitive. Moreover, the extinction factor of the own incident light of the device of the invention reduces considerably the noise accompanying the fluorescent signal.

Finally, this implementation of the present invention with fluorescence microscopy enables to recognise, among identical fluorescent objects, those which depolarise light, which corresponds to a very peculiar environment of the molecules.

This implementation is particularly efficient for the observation of surfaces immersed in a fluorescent medium. It is also very advantageous for reading the fluorescence signal of the biochips, including the observation of hybridization kinetics.

The invention also concerns a measuring method wherein:
the display device is cut parallel to the direction X into two elements,
the thin film is deposited on one of these elements,
both elements are placed between a cross-reflected polarizer and analyser under a polarising microscope illuminated by polychromatic light, in order to form coloured interference fringes on each of the elements,
the offset of the fringes formed respectively in each of the elements is measured in order to deduce therefrom the properties of the layer deposited on one of them.

The invention concerns moreover a display device of a sample as designated above, wherein the substrate is the bottom of a Petri box.

The invention concerns moreover a device for display of a sample as designated above, wherein the sample is a multisensor matrix, whereas each block or wafer of the matrix may form the last layer of the stack. This multisensor can be a bacteria chip, a virus chip, an antigen chip, an antibody chip, a protein chip, a DNA chip, an RNA chip or a chromosome chip, the device constituting then a parallel reading device.

The invention also concerns a method for ellipsometric measurement of a sample with spatial resolution under polarising microscope forming a picture of the sample wherein:
the sample is irradiated by an illuminating beam linearly polarised via an aperture diaphragm,
the light reflected by the sample is analysed by a polarizer-analyser, characterised by the relative orientation $\phi$ of its polarisation direction relative to that of the polarizer,
the intensity reflected is modulated by the relative rotation of the polarisation of the illuminating beam and of the polarizer-analyser.

According to this method:
the aperture diaphragm of the illuminating beam is a ring centred on the axis of the beam delineating a single angle of incidence,
the average reflected flux $\phi_M(x,y)$ and its modulation amplitude $\phi_m(x,y)$ are measured simultaneously at each point of the picture obtained of the sample,
the measurements $\phi_M(x,y)$ and $\phi_m(x,y)$ are processed in order to deduce therefrom simultaneously at each point of the sample two combinations of the ellipsometric parameters $\psi(x,y)$ and $\Delta(x,y)$ and of the reflection coefficient $|r_s|^2(x,y)$ on the basis of the formulae $$\frac{1}{2}|r_s|^2(1+\tan^2\psi) = \phi_M$$

and $$\frac{1}{2}|r_s|^2(\tan^2\psi - 2\tan\psi\cos\Delta) = \phi_m$$

the measurements $\phi_M(x,y)$ and $\phi_m(x,y)$ are processed in order to deduce therefrom the combination $\sin(2\psi)\cos$ of the single ellipsometric parameters $\psi(x,y)$ and $\Delta(x,y)$ on the basis of the formula:

$$\phi_m = \phi_M(1-\sin(2\psi)\cos\Delta)$$

Possibly, in a measuring step:
the orientation of the analyser relative to the polarizer is set to a value different from $\pi/2$ modulo $\pi$,
the aperture diaphragm of the illuminating beam is a slot adjustable around the optical axis of the microscope superimposed on a ring delineating a single angle of incidence,
the intensity of the reflected beam is measured for at least two different and non-redundant orientations $\phi$ of the slot,
these measurements of intensity are processed based on the relation:

$$I = A_i^2 \begin{bmatrix} |r_p|^2\cos^2\varphi\cos^2(\phi-\varphi) + |r_s|^2\sin^2\varphi\sin^2(\phi-\varphi) + \\ (r_p r_s^* + r_p^* r_s)\frac{\sin 2\varphi \sin(2\phi-2\varphi)}{4} \end{bmatrix}$$

the values of both ellipsometric angles $\psi(x,y)$ and $\Delta(x,y)$ and those of the reflection coefficient modules $|r_p|$ and $|r_s|$ are deduced therefrom, simultaneously at each point of the sample.

Possibly, in a complementary step:
the analyser is fixed in an orientation non-perpendicular to the polarizer, for example $\phi=0$,
the aperture diaphragm of the illuminating beam is a slot adjustable around the optical axis of the microscope superimposed on a ring delineating a single angle of incidence,
the intensity reflected for both orientations $\phi=0$ and $\phi=\pi/2$ of the slot is measured,
these measurements of intensity are processed to obtain $\tan\psi$ while taking a square root of their ratio according to the three formulae:

$$I = A_i^2|r_p|^2\cos^2\phi \quad \text{for} \quad \varphi = 0 \text{ modulo } \pi$$

$$I = A_i^2|r_s|^2\sin^2\phi \quad \text{for} \quad \varphi = \frac{\pi}{2} \text{ modulo } \pi$$

$$\tan\psi = \left|\frac{r_p}{r_s}\right|$$

Possibly, in a measuring step
the orientation of the analyser relative to the polarizer is set to a value different from $\pi/2$ modulo $\pi$,
the intensity reflected is modulated by the rotation of the diaphragm D around the optical axis,
the average reflected flux $\phi_M(x,y)$ and its modulation amplitude $\phi_m(x,y)$ are measured simultaneously at each point of the sample,
the measurements $\phi_M(x,y)$ and $\phi_m(x,y)$ are processed in order to deduce therefrom both ellipsometric angles $\psi(x,y)$ and $\Delta(x,y)$ and the modules $|r_p|$ and $|r_s|$ of the reflection coefficients based on the relation:

$$I = A_i^2 \begin{bmatrix} |r_p|^2\cos^2\varphi\cos^2(\phi-\varphi) + |r_s|^2\sin^2\varphi\sin^2(\phi-\varphi) + \\ (r_p r_s^* + r_p^* r_s)\frac{\sin 2\varphi \sin(2\phi-2\varphi)}{4} \end{bmatrix}$$

Possibly, in a complementary step:
the orientation of the analyser relative to the polarizer is set to $\phi=0$, the intensity reflected is modulated by the rotation of the diaphragm D around the optical axis, the average reflected flux $\phi_M(x,y)$ and its modulation amplitude $\phi_m(x,y)$ are measured simultaneously at each point of the sample, the measurements $\phi_M(x,y)$ and $\phi_m(x,y)$ are processed in order to deduce therefrom both ellipsometric angles $\psi(x,y)$ and $\Delta(x,y)$ and the modules $|r_p|$ and $|r_s|$ of the reflection coefficients based on the relation:

$$I = A_i^2 \left[ \begin{array}{l} |r_p|^2 \cos^2\varphi \cos^2(\phi-\varphi) + |r_s|^2 \sin^2\varphi \sin^2(\phi-\varphi) + \\ [r_p r_s^* + r_p^* r_s] \dfrac{\sin 2\varphi \sin(2\phi - 2\varphi)}{4} \end{array} \right].$$

The invention also concerns a method for ellipsometric measurement of a sample with spatial resolution under polarising microscope forming a picture of the sample, wherein:

the sample is irradiated by an illuminating beam linearly polarised via an aperture diaphragm, the light reflected by the sample is analysed by a polarizer-analyser, characterised by the relative orientation $\phi$ of its polarisation direction relative to that of the polarizer, the intensity reflected is modulated by the relative rotation of the polarisation of illuminating beam and of the polarizer-analyser, According to this method:

the aperture diaphragm of the illuminating beam is a disk centred on the axis of this beam, the average reflected flux $\phi_M(x,y)$ and its modulation amplitude $\phi_m(x,y)$ are measured simultaneously at each point of the picture obtained of the sample, the measurements $\phi_M(x,y)$ and $\phi_m(x,y)$ are processed in order to deduce therefrom simultaneously at each point of the sample two combinations of the effective ellipsometric parameters $\psi_{eff}(x,y)$ and $\Delta_{eff}(x,y)$ and of the effective coefficient reflection $|r_{s\,eff}|^2(x,y)$ on the basis of the formulae:

$$\frac{1}{2}|r_s|^2(1+\tan^2\psi_{eff}) = \phi_M$$

et $$\frac{1}{2}|r_s|^2(\tan^2\psi_{eff} - 2\tan\psi\cos\Delta_{eff}) = \phi_m$$

the measurements $\phi_M(x,y)$ and $\phi_m(x,y)$ are processed in order to deduce therefrom the combination $\sin(2\psi)\cos$ of the single effective ellipsometric parameters $\psi_{eff}(x,y)$ and $\Delta_{eff}(x,y)$ on the basis of the formula:

$$\sin 2\psi_{eff} \cos\Delta_{eff} = 1 - \frac{\phi_m}{\phi_M}$$

The invention also concerns a device for ellipsometric measurement under microscope with lateral spatial resolution.

According to this device:

it only comprises a single polarizer placed between the illuminating mirror and the sample on either side of the lens, it comprises a slot revolving in the plane of its aperture diaphragm, possibly superimposed on a ring diaphragm enabling to extract the ellipsometric parameters of the sample using at least three measurements for three different orientations of the slot and of the formula:

$$I = A_i^2 |r_s|^2 \left\{ \tan^2\psi\cos^4\varphi + \sin^4\varphi - \frac{\sin^2 2\varphi}{2}\tan\psi\cos\Delta \right\}$$

applied to these three measurements, wherein the parameters $r_s$, $\psi$ and $\Delta$ may be effective parameters derived from averages over all the angles of incidence present:

$$I = A_i^2 \left\{ \begin{array}{l} |r_p|^2 \cos^2\varphi \cos^2(\Phi-\varphi) + |r_s|^2 \sin^2\varphi \sin^2(\Phi-\varphi) + \\ [r_p r_s^* + r_p^* r_s] \dfrac{\sin 2\varphi \sin(2\Phi - 2\varphi)}{4} \end{array} \right\}$$

According to this device:

the polarizer and the analyser have a set relative orientation, the aperture diaphragm is a hole or a ring, the picture of the rear focal plane of the lens is formed in the focal plane object of the ocular by a Bertrand lens, a CCD camera is positioned in this plane, the measurement of the intensity obtained at each point of the CCD camera is processed thanks to the general formula:

$$I(\varphi, \Phi, \theta, \lambda) = $$
$$A_i^2 \left\{ \begin{array}{l} |r_p(\theta,\lambda)|^2 \cos^2\varphi \cos^2(\Phi-\varphi) + |r_s(\theta,\lambda)|^2 \sin^2\varphi \sin^2(\Phi-\varphi) + \\ [r_p(\theta,\lambda)r_s^*(\theta,\lambda) + r_p^*(\theta,\lambda)r_s(\theta,\lambda)] \dfrac{\sin 2\varphi \sin(2\Phi - 2\varphi)}{4} \end{array} \right\}$$

in order to obtain directly the set of the ellipsometric parameters of the sample.

According to this device:

a modulation of the intensity reflected is obtained by a rotation relative of the analyser and of the polarizer, the aperture diaphragm is a hole or a ring, the picture of the rear focal plane of the lens is formed in the focal plane object of the ocular by a Bertrand lens, a CCD camera or possibly tri-CCD is positioned in this plane, the measurement of the intensity obtained at each point of the CCD camera or possibly at each point and for each colour component of the tri-CCD camera is processed thanks to the general formula:

$$I(\varphi, \Phi, \theta, \lambda) = $$
$$A_i^2 \left\{ \begin{array}{l} |r_p(\theta,\lambda)|^2 \cos^2\varphi \cos^2(\Phi-\varphi) + |r_s(\theta,\lambda)|^2 \sin^2\varphi \sin^2(\Phi-\varphi) + \\ [r_p(\theta,\lambda)r_s^*(\theta,\lambda) + r_p^*(\theta,\lambda)r_s(\theta,\lambda)] \dfrac{\sin 2\varphi \sin(2\Phi - 2\varphi)}{4} \end{array} \right\}$$

in order to obtain directly the set of the ellipsometric parameters of the sample.

According to this device:
the picture of the rear focal plane of the lens is formed in the focal plane object of the ocular by a Bertrand lens,
a CCD camera is positioned in this plane,
the measurement of the intensity obtained at each point of the CCD camera is processed thanks to the general formula:

$$I(\varphi, \Phi, \theta, \lambda) = A_i^2 \left\{ \begin{array}{l} |r_p(\theta, \lambda)|^2 \cos^2\varphi \cos^2(\Phi - \varphi) + |r_s(\theta, \lambda)|^2 \sin^2\varphi \sin^2(\Phi - \varphi) + \\ [r_p(\theta, \lambda) r_s^*(\theta, \lambda) + r_p^*(\theta, \lambda) r_s(\theta, \lambda)] \dfrac{\sin 2\varphi \sin(2\Phi - 2\varphi)}{4} \end{array} \right\}$$

in order to obtain directly the set of the ellipsometric parameters of the sample.

The camera is a tri-CCD colour camera and the measurement of the intensity at each point is performed and processed for each of the colours.

Advantageously, the object studied is placed on a substrate. The thickness e of the layer of the stack in contact with the object is such that the complex reflection coefficients $r_p$ and $r_s$ of the substrate verify the condition $d^2/de^2 [Ln|r_p+r_s|]=0$.

Preferably, the object is placed on a substrate whereof the optical properties are such that the minimum value taken by the quantity $|r_p+r_s|$ over the set of values of e is as small as possible.

BRIEF DESCRIPTION OF THE DRAWINGS

An embodiment of the invention will be described more accurately with reference to the appended drawings whereon FIGS. 1 and 2 define the polarising parameters of the light p and s relative to the propagation vector k and the orientation parameters, incidence and azimuth θ and φ of the radii in the optical system;

FIG. 4 is a diagram of the polarising microscope implemented according to the invention ; wherein FIGS. 4A and 4B are representations of devices usable according to the invention; the analogous elements are represented with the same numeric reference.

DETAILED DESCRIPTION OF THE INVENTION

Figure 1:
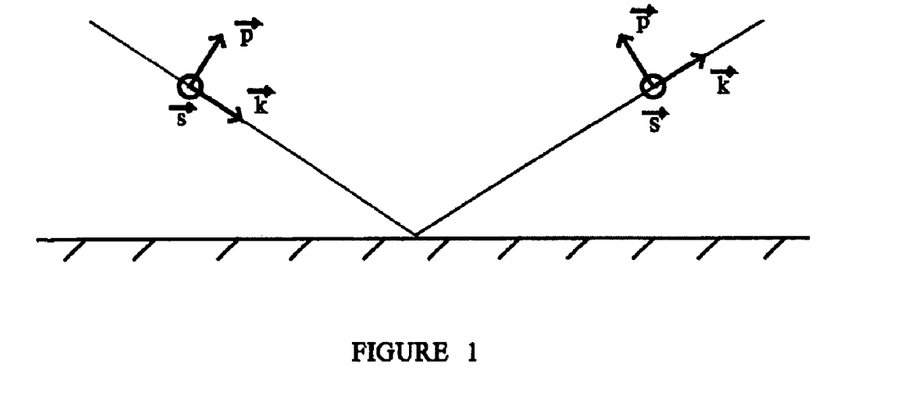
Figure 2:
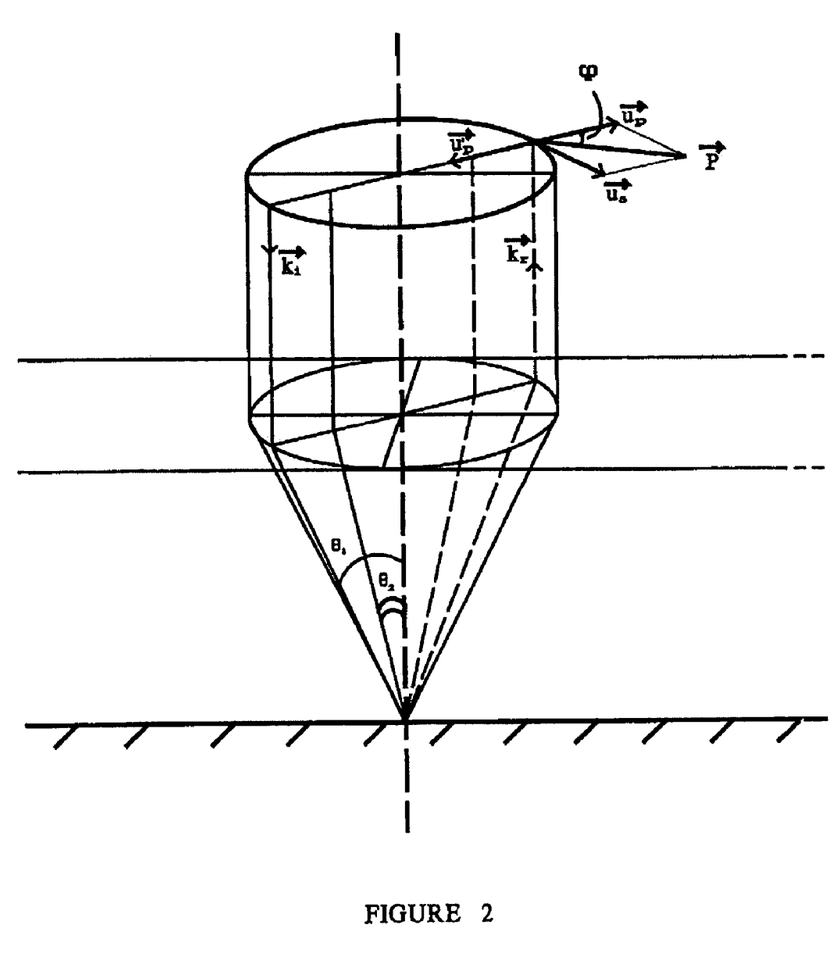

The description of the invention will be made using the notations of FIGS. 1 and 2, where $\vec{p}$ is the polarisation vector of the light carried by a radius of incidence angle θ on the sample.

Figure 3:
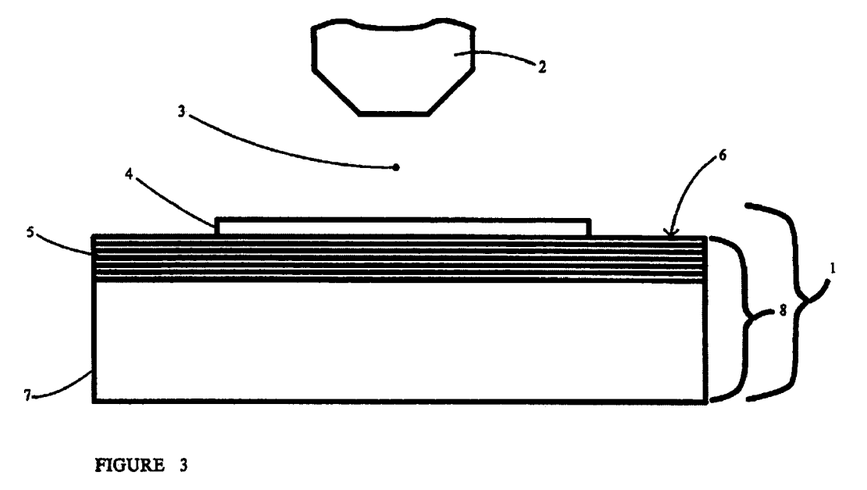
FIG. 3 shows the sample relative to the lens of the microscope.

Besides, by —sample 1— is meant the assembly acting on the measurement. This sample is separate from the lens 2 by an incident medium 3, it comprises, starting from the incident medium, a studied object 4 (the one that should be displayed), a stack 5 of layers whereof the outermost layer 6 is the layer in contact with the sample, and a base 7. The stack of layers and the base form the substrate 8.

A sample 1, supposedly plane and isotropic, is therefore placed under a reflection-operating optical microscope. The microscope is fitted with a lens 10 and a Köhler-type illuminating system, comprising at least two lenses 12 and 13 and a aperture diaphragm or pupil 11 conjugated by the lens 13 of the rear focal plane of the lens 10, represented by a dotted line on FIG. 4A. The polarizer P polarises the light directed toward the sample by the semi-reflecting plate 15. The direction of the polarizer P is used as a reference. The light sent by the object is subject to an analyser A.

Figure 4:
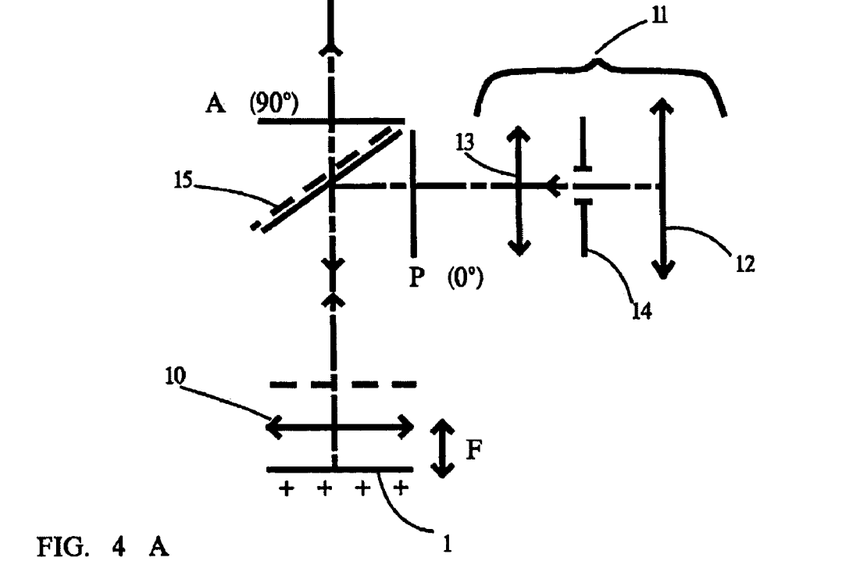

FIG. 4B correspond to the implementation of a differential interferential contrast (DIC) microscope, it comprises a polarising element 16 which is either a Wollaston biprism or a Nomarksi prism and compensator.

As it is known besides, it is also possible to replace the linear polarisations with circular polarisations.

Then, instead of cross-connected polarizers and analysers, there will be the semi-transparent mirror, a first polarizer, a quarter wave plate (λ/4), the lens, the sample, then as a feedback, the lens again, the plate λ/4, the polarizer mentioned above and the semi-transparent mirror.

In the case of the differential interferential contrast (DIC) microscope, there will be then the semi-transparent mirror, a polarizer, the polarising element, a plate λ/4, the lens, the sample, then as a feedback, the lens again, the plate λ/4, the polarising element, the polarizer mentioned above and the semi-reflecting mirror.

The angle of incidence of a radius is θ. The microscope is fitted with a linear polarizer and an analyser situated on either side of the sample on the path of the light. The illumination is episcopic and monochromatic. The analyser is revolving and forms an angle φ with the polarizer. The normalised reflected flux $\Phi_N$ is measured as the ratio of the reflected flux to a reference flux. The reference flux is that which would be obtained on the same instrument adjusted similarly in the absence of a polarizer and of an analyser with a hypothetical perfectly reflecting sample. The perfectly reflecting sample is defined by its Fresnel complex coefficients for parallel (p) and perpendicular (s) polarisations as $r_p=r_s=1$. For any angle φ:

$$\Phi_N(\theta, \phi) = \cos^2\phi (|r_p|^2 + |r_s|^2) - \frac{\cos 2\phi}{4} |r_p + r_s|^2 \qquad \text{E1}$$

In the particular case when the polarizer and the analyser are cross-connected (φ=π/2), this formula is reduced to:

$$\Phi_N\left(\theta, \frac{\pi}{2}\right) = \frac{|r_p + r_s|^2}{4} \qquad \text{E2}$$

The second member of the formula (E1) may be construed directly. It consists of two terms:

The first, $\cos^2\phi(|r_p|^2+|r_s|^2)$, is the product of an extinction coefficient and of an intensity reflection coefficient that will now be designated as reflectivity. Such reflectivity may be qualified as "incoherent average reflectivity" since it would be obtained by ignoring the interferences between $r_p$ and $r_s$, i.e. between the parallel and perpendicular reflected components, and by averaging all the possible azimuths φ, i.e. over all the possible orientations of the plane of incidence relative to the direction of the polarizer. Reduced to its first term, the equation (E1) would then provide the reflection obtained by reversing the order of the sample and of the analyser on the path of the light, since the surface only plays here the part of an absorbing element. This first term disappears totally when $\phi=\pi/2$: between cross-connected polarizer and analyser, and in the absence of (de)polarising elements, nothing goes through.

The second term of the equation (EI) describes the interference between $r_p$ and $r_s$. It will be called "coherent reflectivity". It represents the depolarisation of the incident beam by the surface, which converts the linear incident polarisation into an elliptic polarisation. This ellipticity is different for each azimuth, i.e. for each plane of incidence defined by its angle $\phi$ with the direction of the polarizer, and this second term describes the average reflectivity which results therefrom for the conical geometry of the irradiation. It disappears for $\phi=\pi/4$, where the contributions of all the azimuths negate one another, and also for $r_p=-r_s$. It reduces the total reflectivity between parallel polarizer and analyser, and increases them when they are cross-connected.

The display technique, object of the present invention, processes directly this second term. We select $\phi=\pi/2$, and the second term of the equation (EI) remains the only one present. The extinction or, in a more elaborated version, the quasi extinction of the incoherent reflectivity is one of the foundations of the invention. What is called "coherent reflectivity" may also be called "ellipsometric reflectivity" since it results from ellipticities (functions of the azimuth $\phi$) of the reflected polarisation.

An expression equivalent to (E1) is:

$$\Phi_N(\theta, \phi) = \frac{1}{2}(|r_p|^2 + |r_s|^2) + \frac{\cos 2\phi}{4}|r_p - r_s|^2 \quad \text{E3}$$

This expression enables to compare the signal obtained in the presence of polarising elements with the signal obtained in the absence of polarising elements, i.e. in non-polarised light, which is provided by the first term only. It will be noted as:

$$\Phi_N(\theta, NP) = \frac{1}{2}(|r_p|^2 + |r_s|^2) \quad \text{E4}$$

In the presence of the polarizers, it is still possible to access experimentally such quantity by imposing $\phi=\pi/4$, as shown on the equation E3.

To display the edge of a studied object 4 in the form of a thin film placed on the surface, the intensities collected are processed by observing the film and the bare surface which are noted $I_F$ and $I_S$. They are proportional to the corresponding normalised fluxes The contrast of the edge of the film is:

$$C = \frac{I_F - I_S}{I_F + I_S} = 1 - \frac{2}{1 + \frac{I_F}{I_S}} \quad \text{E5}$$

To display the film correctly, C should be optimised and therefore the $I_F/I_S$ ratio should be made maximal ($I_S \to 0$, to tend toward a contrast of 1) or minimal ($I_F \to 0$, to tend toward a contrast of −1). It is then necessary to extinguish either the surface or the film. Thus, a sensitive process rests on the one hand on a correct extinction and on the other hand on a selective extinction.

Our technique combines two extinction factors:
i) the polarizer and the analyser which are cross-connected or almost cross-connected,
ii) an antireflection substrate for this mode of observation.

The equation (E3) underlines the double nature of our extinction: the cross-connected polarizer and analyser extinguish the first term of the second member, our antireflection substrate extinguishes the second. It can then be defined as an antireflection substrate for coherent reflectivity. It is the second foundation of our display technique.

But good extinction does not suffice for a sensitive display. $I_F$ or $I_S$ should be extinguished, but not both at the same time. As the film displayed is very thin, as therefore all its physical parameters hardly disturb those of the bare surface, it means that the extinction must be critical. In other words, the extinction must be lost for a very small modification of the surface. This critical element of the antireflection quality of our substrate is the third foundation of our display technique.

The performances of a display process may be quantified by the contrast obtained when the film observed becomes extremely thin. In such a case, $I_F$ and $I_S$ becomes neighbours and $dI=I_F-I_S$ is close to a differential element.

C can then be written as $$C = \frac{1}{2}\frac{dI}{I_S} = \frac{1}{2}\frac{I}{I_S}\frac{dI}{de}\Delta e$$

where $\Delta e$ is the thickness of the film which can be assumed when the optical index is identical to that of the upper layer, and where dI/de is the derivate of the intensity reflected by the bare substrate relative to the thickness e of the last layer of the stack. In the case where the substrate is composed of a solid base covered with a single dielectric layer, e is therefore the thickness of this layer. Taking an identical index for the film and for the last dielectric layer is not compulsory, but it simplifies the explanation and shows that our process does not take advantage of the reflection between the film and the substrate. The film is therefore considered here as a simple thickness fluctuation of the outermost layer.

The sensitivity of our technique is expressed in Angströms$^{-1}$ as the ratio of C to $\Delta e$:

$$\frac{C}{\Delta e} = \frac{1}{2}\frac{dLnI}{de} = cste + \frac{dLn|r_p - r_s|}{de} \quad \text{E7}$$

The expression of $r_p$ and $r_s$ for a solid covered with a single layer is conventional (ref. AZZAM for instance):

$$r(k) = \frac{r_{01(k)} + r_{12(k)}e^{-2j\beta 1}}{1 + r_{01(k)} \times r_{12(k)}e^{-2j\beta 1}} \quad \text{E8}$$

with k=either s or p, according to the polarisation considered and with $$\beta_1 = 2\pi\frac{N_1 e}{\lambda}\cos\theta_1,$$

the index 1 referring to the layer, the index 2 to the base and the index 0 to the incident medium.

This equation enables to write:

$$\sigma \equiv r_p + r_s = \frac{\sigma_{01} + \sigma_{12}(1 + \Pi_{01})e^{-2j\beta 1} + \sigma_{01}\Pi_{12}e^{-4j\beta 1}}{(1 + r_{01(p)}r_{12(p)}e^{-2j\beta 1})(1 + r_{01(s)}r_{12(s)}e^{-2j\beta 1})} \quad \text{E9}$$

where $\sigma_{ij}$ and $\Pi_{ij}$ represent respectively the sum and the product of $r_{ij(p)}$ and $r_{ij(s)}$.

The sum $\sigma$ is a periodical function of the optical thickness $N_1 e$ of period $\lambda/2$. Its module $|\sigma|$ shows generally two minima and two maxima per period. The same goes for $Ln|\sigma|$. The function $|\sigma|$ being moreover a delineated function, it remains very regular and its derivate relative to $e$ is never very significant. Conversely, the function $Ln|\sigma|$ diverges when $|\sigma|$ tends toward zero and the sensitivity given by the equation E7 becomes very significant in absolute value on either side of the minimum when the extinction is total. The contrast is always negative on the left-hand side of a minimum and positive on the right-hand side. Consequently the condition to obtain a minimum will be designated as a "condition of contrast reversal".

As a summary, the rapid contrast reversals inversions correspond therefore to the minima of $|r_p+r_s|$ relative to $e$, and the very rapid contrast reversals are obtained when this minimum of $|r_p+r_s|$ tends toward 0.

The equation (E3) underlines the significance of the use of a fluorescence microscope: in the presence of a fluorescence signal, the depolarised component of this fluorescence is added to the right-hand side member of the equation (E3) without altering the extinction of both other terms. The signal/noise ratio is therefore increased. This is also transposable to a Raman signal.

The invention also concerns an ellipsometric measurement method which may also operate without needing to resort to a particular substrate:

The ellipsometric angles $\psi$ and $\Delta$ are defined by:

$$\frac{r_p}{r_s} = \tan\Psi e^{j\Delta} \quad \text{E10}$$

Two equations selected arbitrarily among the four following ones suffice to establish the matches which will be useful between reflectivities and ellipsometric parameters:

$$|r_p|^2 + |r_s|^2 = |r_s|^2(1 + \tan^2\psi) \quad \text{E11}$$

$$|r_p + r_s|^2 = |r_s|^2(1 + \tan^2\psi + 2\tan\psi\cos\Delta) \quad \text{E12}$$

$$|r_p - r_s|^2 = |r_s|^2(1 + \tan^2\psi - 2\tan\psi\cos\Delta) \quad \text{E13}$$

$$r_p r_s^* + r_p^* r_s = 2|r_s|^2\tan\Psi\cos\Delta \quad \text{E14}$$

The first of these equations shows that the ellipsometric parameter $\psi$ is accessible by the measurement of the incoherent reflectivity. Each of the other three shows that the determination of the second ellipsometric parameter, $\Delta$, requires moreover to measure the coherent reflectivity (or a combination of both reflectivities). Accessing the coherent reflectivity signal enables to determine $\psi$ and $\Delta$.

The measurement takes place in two steps:
i) The first is based upon the rotation of the analyser. The picture of the sample is analysed by a CCD camera or any other two-dimensional detector. The equation E3 shows that the signal reflected oscillates in a sine wave fashion around the incoherent reflectivity with an amplitude $|r_p - r_s|^2$ and a period $\pi$ on the angle $\phi$. Various procedures, requiring at least two measurements, enable to obtain two combinations of the three parameters $|r_s|^2$, $\tan\psi$, and $\cos\Delta$, for example $|r_s|^2(1 + \tan^2\psi)$ and $2|r_s|^2\tan\psi\cos\Delta$. This enables already to determine the combination $\sin 2\psi\cos\Delta$ of the single ellipsometric parameters, but does not suffice to determine $\Delta$ and $\psi$ separately.

ii) The second step requires breaking the radial symmetry of the illumination, which may be performed in two ways:
either by modifying physically the geometry of the aperture diaphragm, which must become a slot or a cross composed of two perpendicular slots, or an angular sector $\delta\phi$ (modulo $\pi$) with aperture strictly smaller than $\pi/4$, whereof the apex is confused with the optical axis or the association of two or four identical angular sectors, spaced regularly around the optical axis of the microscope, capable as the analyser to revolve around the optical axis of the microscope, or by analysing the distribution of intensity present in a conjugated plane of the aperture diaphragm placed on the path of the reflected light, the microscope being in Koehler illumination. The microscope being fitted with a CCD camera in order to receive the picture of the sample, this analysis may take place very simply by interposing a Bertrand lens between the lens and the pupil of the camera. It is therefore a conoscopic measurement. The interest of this solution, easy to be implemented, is that the angle of incidence $\theta$ and the azimuth $\phi$ are, in the conjugated plane, two parameters which can be separated geographically and that it is then possible to access the whole function $\Phi_M(\theta,\phi,\lambda)$, $\lambda$ designating the wave length of the luminous beam. The range of aperture angles kept may be adjusted, the azimuth explored, or the illumination filtered by digital means. This solution also enables, in the absence of the Bertrand lens, to carry out the first step of the analysis simultaneously in several regions of a heterogeneous sample, and hence to determine by parallel measurement the quantity $(\sin 2\psi \cos \Delta)(x,y)$. For complete analysis with the Bertrand lens, it is however necessary to select a homogeneous region of the sample by the use of a field diaphragm or of a confocal geometry. This solution does not enable therefore complete parallel analysis of the different points of the sample. The first solution, conversely (diaphragm with broken radial symmetry), enables total parallel analysis since the picture of the sample is always kept on the CCD camera.

The intensity reflected I when a very small angular sector $\delta\phi$ selects a particular azimuth $\phi$ on the illuminating cone, provided by the equivalent of the equations EI to E4 is now:

$$I = A_i^2 \left[ \begin{array}{l} |r_p|^2 \cos^2\varphi\cos^2(\phi-\varphi) + |r_s|^2\sin^2\varphi\sin^2(\phi-\varphi) + \\ [r_p r_s^* + r_p^* r_s]\frac{\sin 2\varphi \sin(2\phi - 2\varphi)}{4} \end{array} \right]$$

Generally speaking, this intensity is a periodical function $\phi$ of period $\pi$ and also comprises terms of period $\pi/2$.

If the relative orientation of the analyser and of the polarizer is set and:
if the slot is driven by a uniform rotational movement around the optical axis at the frequency $\omega$, the intensity reflected by each point of the sample is modulated and this modulation enables to extract different combinations of the quantities $|r_s|$, $\psi$ and $\Delta$ requested. To do so, several techniques can be implemented, notably photometric-type techniques processing time-related intensity averages and extreme amplitudes or synchronous detection techniques enabling to compare the amplitudes and the phases of the components of the intensity reflected at $2\omega$ and at $4\omega$;

if the orientation of the slot is adjustable manually, the intensities collected may be measured for several orientations of the slot, two at least, in order to deduce from the general formula above, the values of different combinations of the parameters $|r_s|$, $\psi$ and $\Delta$, which enables to determine completely the values of these parameters;

if the analyser is driven by a uniform rotational movement around the optical axis, the signal I is modulated with a period $\pi$ (over $\phi$) and the measurement of I for different values of $\phi$ becomes more accurate;

if finally the analyser and the slot are both driven by uniform rotation, at different frequencies, the function $I(\phi, \varphi)$ can be recognised completely and the parameters $|r_s|$, $\psi$ and $\Delta$ can be determined with very great accuracy by a conventional three-parameter numeric adjustment procedure.

In the simplest particular case when the angle $\phi$ is set and when the measurement of I is performed for both orientations $\phi=0$ (modulo $\pi$) and $\phi=\pi/2$ (modulo $\pi$) of the slot, the following can be obtained respectively:

$\Phi_N(\theta,\phi,\varphi=0)=1/2|r_p|^2 \cos^2 \phi$ and $\Phi^N(\theta,\phi,\varphi=\pi/2)=1/2|r_s|^2 \cos^2 \phi$ It suffices therefore to take the root of the ratio of both these intensities to obtain the quantity tan $\psi$. This measurement combined to both previous ones enables therefore to determine completely $|r_s|^2$, $\psi$, and $\Delta$, and hence also $|r_p|^2$.

It should be noted that the determination of the single parameters $\psi$ and $\Delta$ can be obtained by using exclusively ratios with measured intensities, and consequently does not require using any reference substrates.

An interesting particular case is that when $\Phi=0$ which corresponds to a parallel polarizer and analyser and which can therefore be deduced from that of a single polarizer arranged between the illuminating mirror and the lens or even between the lens and the sample. The intensity reflected can be written in such a case as:

$$I = A_i^2 \left\{ |r_p|^2 \cos^4 \varphi + |r_s|^2 \sin^4 \varphi - \frac{\sin^2 2\varphi}{2} |r_s|^2 \tan\psi \cos\Delta \right\}$$

This demonstrates that with a revolving diaphragm composed of a slot, of a cross consisting of two perpendicular slots crossing one another on their axis, of an angular sector whereof the apex is placed on the optical axis of the microscope and of azimuth amplitude smaller than 45 degrees, or of the association of two or four angular sectors of the same type, arranged regularly around the optical axis, which diaphragm is possibly superimposed to a ring to delineate a single angle of incidence, it suffices to carry out three measurements of intensity reflected with three different and non-redundant orientations of the diaphragm in order to deduce therefrom the set of the ellipsometric parameters of the sample. For instance, in case when the diaphragm is a slot or a very small angular sector marked by its orientation $\phi$, the intensity reflected at each point of the picture of the sample becomes:

$$I_1 \equiv I(\varphi=0) = A_i^2|r_p|^2 = A_i^2|r_s|^2(1+\tan^2\psi) \quad \text{for } \varphi=0$$

$$I_2 \equiv I\left(\varphi=\frac{\pi}{2}\right) = A_i^2|r_s|^2 \quad \text{for } \varphi=\pi/2$$

$$I_3 \equiv I\left(\varphi=\frac{\pi}{4}\right) = 2A_i^2|r_s|^2\tan\psi\cos\Delta \quad \text{for } \varphi=\pi/4$$

It suffices therefore to calculate the ratio $$\frac{I_1}{I_2}$$

in order to deduce therefrom tan $\psi$, then the ratio $$\frac{I_3}{I_2}$$

in order to deduce therefrom cos $\Delta$.

This example illustrates:

how the measurement of three intensities with three different orientations of the slot enables to determine the set of the ellipsometric parameters by using exclusively intensity ratios, hence without an appended calibration;

how a modulation of the intensity reflected which includes these three measurements, but also others, enables to obtain the same information with increased accuracy;

how an ellipsometer under optical microscope or under binocular magnifying glass may be realised by using a single polarizer and a revolving slot.

When exposing the measurement process, equations valid for a single angle of incidence $\theta$ have been used. As $|r_s|^2$, $\psi$, and $\Delta$ depend on $\theta$, the following options are considered: either access these quantities for a single angle $\theta$ by using an annular aperture diaphragm, or access quantities averaged over a range of incidence angles $[\theta_{min}, \theta_{max}]$, with $\theta_{min}=0$, most often.

The same formulae apply to effective quantities, allocated below with an index "eff", defined on the basis of averages over $\theta$. It is then necessary to state:

$$|r_p|^2_{eff} = \langle |r_p|^2 \rangle_\theta$$

$$|r_s|^2_{eff} = \langle |r_s|^2 \rangle_\theta$$

$$\tan\psi_{eff} = \frac{|r_p|_{eff}}{|r_s|_{eff}}$$

$$\cos\Delta_{eff} = \frac{\langle |r_s|^2 \tan\psi \cos\Delta \rangle_\theta}{|r_s|_{eff} \cdot |r_p|_{eff}}$$

to write the intensity reflected as:

$$I = A_i^2 \left[ \begin{array}{l} |r_p|^2_{eff}\cos^2\varphi\cos^2(\phi-\varphi) + |r_s|^2_{eff}\sin^2\varphi\sin^2(\phi-\varphi) + \\ 2|r_s|^2_{eff}\tan\psi_{eff}\cos\Delta_{eff}\dfrac{\sin 2\varphi \sin(2\phi-2\varphi)}{4} \end{array} \right]$$

The measurement of I enables therefore to determine the effective quantities and, in particular, the ellipsometric angles $\psi_{eff}$ and $\Delta_{eff}$, which may be compared with values calculated in order to deduce therefrom the properties of the object or of the sample, as it is done conventionally with the single incidence ellipsometric angles.

Indeed, the interest of the method lies especially in carrying out ellipsometric measurements under microscope in order to combine ellipsometric measurement and imaging. It should therefore be considered that the natural geometry of the illumination is a light cone around the normal. Still, the ellipsometric parameters hardly vary for small incidences. This explains why the ellipsometry is a technique only sensitive at high angles of incidence. The counterpart in our method is that the average performed on the illuminating cone garbles only sligthly the signal exploitable. In the absence of optimised substrate, the drawback of the ellipsometric measurement under microscope is that its sensitivity is poor. But in the presence of the optimised substrates as suggested, the sensitivity of the measurement to the physical parameters of the sample becomes excellent again, comparable in fact with that of conventional measurements around the Brewster angle, whereas the signal exploited remains little sensitive to the angle of incidence. This can be explained because between cross-connected polarizer and analyser, the extinction of the coherent reflectivity is still complete in normal incidence, to the extent that only the non-zero incidences take part to the construction of the signal exploited. With the conditions of a good extinction for non-zero incidences, the extinction is good over the set of incidences of the illuminating cone.

It is possible to optimise the thickness of the last layer for any materials.

Indeed, it has been shown that the function $|\sigma(e)|=|r_p+r_s|$ still has more or less marked minima, which correspond to the conditions of contrast reversal. The contrast is therefore nil for these particular values of e. Being also periodical and continuous, it reaches a minimum on the left-hand side of these values and a maximum on the right-hand side. It is therefore still possible to select the thickness e so that one of these extrema is reached. Regardless of the nature of the substrate, the thickness of the dielectric layer can be optimised by calculating $|\sigma(e)|$. This becomes particularly interesting when getting closer to the critical conditions.

The critical compositions of the substrates are defined by the existence of a solution to the equation $|\sigma(e)|=0$. A critical substrate possesses a layer thickness close to a solution of this equation. A solution to the equation $|\sigma(e)|=0$ corresponds necessarily to a minimum of $|\sigma(e)|$. It is therefore a contrast reversal thickness. The smallest of these values, $e_c$, plays of course a particular part. The other contrast reversal thicknesses are then given by $e_{c,k}=e_c+KN_1\lambda/2$.

According to the equation E9, the equation discussed is:

$$\sigma_{01}+\sigma_{12}(1+\Pi_{01})e^{-2j\beta 1}+\sigma_{01}\Pi_{12}e^{-4j\beta 1}=0 \quad \text{E15}$$

In the case of a stack reduced to a single layer, the values $e_c$ of e are the solutions of the equation E15 derived from of E9:

$$\sigma_{01}+\sigma_{12}(1+\Pi_{01})z+\sigma_{01}\Pi_{12}z^2=0 \quad \text{E16}$$

It possesses two complex solutions z1 and z2 which are functions of the indices of the incident medium, of the layer, of the complex index of the substrate, and of the angle of incidence $\theta 0$ (or in an equivalent fashion, of the angle refracted in the layer, $\theta 1$). The critical conditions are reached when the module of one of both these solutions is equal to 1. This problem is rather simple to be explored numerically.

Analytically, it is possible to develop each of the terms up to the order 4 in $\theta 1$ since each of them depends only little on the angle close to the normal. "Taylor-made" solutions can then be found. In practice, both extreme media are often imposed and it is the index and the thickness of the layer that should be determined. The contrast is then plotted in relation to the thickness for a few random indices and a monotonic variation in the contrast can be observed. It suffices therefore to progress in the direction when things improve until they begin to fall off in quality. From then on, the exploration is resumed around the best value while fine-tuning the index variations. The numerous results published in the literature may also be used for a single layer in terms of $\psi$ and $\Delta$. The situations requested correspond simultaneously to:

$$\tan \psi=1 \text{ and } \Delta=\pi \quad \text{E17}$$

The solutions found numerically are rather well approximated by the empiric formula:

$$N_2 = N_o\left[\frac{N_0}{N_3} + \sqrt{1+\left(\frac{N_0}{N_3}\right)^2}\right] \quad \text{E18}$$

Particularly interesting results are obtained by realising a silicon substrate covered with a single layer meeting the following parameters, the irradiation being preferably monochromatic and of wavelength $\lambda=540$ nm and the angle of aperture of the illumination cone being assumed as 30 degrees:

| $N_o$ | $N_3$ | $N_2$ | e |
|---|---|---|---|
| 1.00 (air) | 3.88 − 0.02 i | 1.343 | 1060 ± 5 Å |
| 1.34 (water) | 3.88 − 0.02 i | 1.749 | 814 ± 5 Å |
| 1.50 (oil) | 3.88 − 0.02 i | 1.945 | 750 ± 10 Å | when $N_o$ is the index of the ambient medium, $N_3$ is the index of the base of the substrate, $N_2$ is the index of the layer and e its thickness.

The optimal thickness e is a linear function of $\lambda$ but cannot be made proportional to $\lambda$. For observations in the air $$\frac{\partial e}{\partial \lambda} = 0.2.$$

The layers with indices 1.74 and 1.945 may be produced by numerous methods, such as the PECVD deposits. The layers with an index of 1.345 are more difficult to realise. They may be formed of a hydrogel, of an aerogel, of a polymer or be heterogeneous, for example formed of blocks with constant thickness and with very small dimensions. It may also be a solution in water, sugar, salt, polymer . . .

Figure 5:
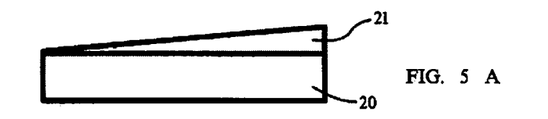
FIG. 5 is a schematic diagram of the thickness direct measuring device according to the invention.

A particularly interesting method for visualising the optical thickness ($N_1 \times e_1$) of a very thin film can be realised with the substrate implemented in the invention as follows, as represented on FIG. 5.

On a base 20 is realised a deposit of a layer 21 of variable thickness in the form of a chamfer (FIG. 5A, FIG. 5B).

This substrate 20 is then cut in order to obtain two identical elements 22, 23 (23 non-represented is then identical to 22) (FIG. 5C).

One of these elements of the thin film 24 to be studied (FIG. 5C) is then covered.

Both these elements under microscope, irradiated with white light using a disk-shaped pupil, are then observed, after having positioned both these elements with respect to one another, in their relative initial position, using a mark, a notch or a wedge 25.

White light fringes 26, 27 are then observed, respectively on each of these elements and their relative offset $\Delta\lambda$ enables to measure the properties of the layer deposited on one of these elements.

The invention is particularly suited to the display of elements contained in multisensors.

Figure 6:
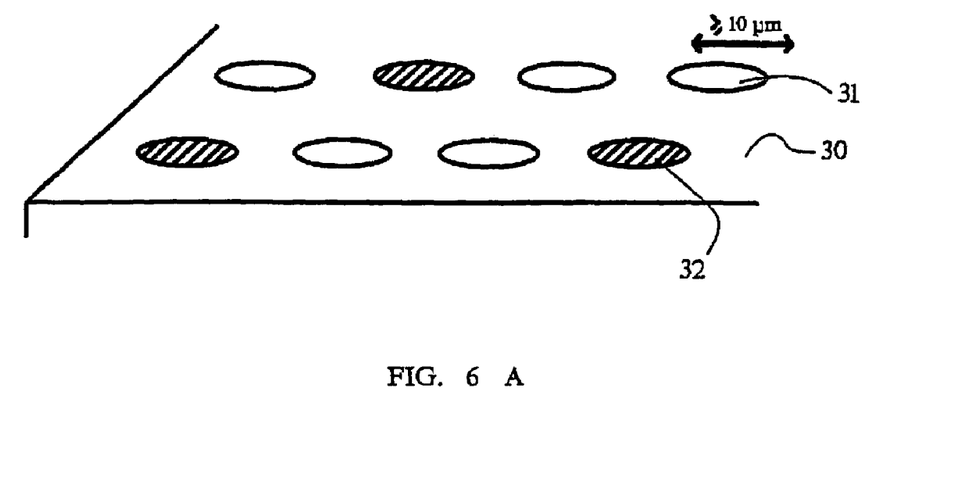
FIGS. 6A and 6B are a diagrammatical representation of the display device of a multisensor implemented in certain embodiments of the invention.

A chemical or biological (biochip) multisensor consists of a base 30 whereon are deposited wafers 31 (=spots) each formed of a different layer capable of fixing selectively a different specie to be recognised within a liquid mixture (biochip) or gaseous (artificial nose), and forming between them a matrix of elements arranged along the surface. Each wafer has a surface area of a few square microns and often a thickness of molecular order of magnitude.

The multisensor is used as follows: it is put in contact with the mixture that should be analysed. Each wafer 31, 32 . . . captures the specie which it can recognise when it is present in the mixture. In situ or after rinsing, the purpose is to discover which blocks 32 have become loaded and which blocks 31 have remained empty to know the composition of the mixture. A fixed specie creates an excessive thickness, which can be visualised at the block, the position of the blocks 31, 32 in the matrix tells about the nature of the specie recognised. This step is the reading step of the multisensor.

Our microscopy method is sensitive enough to show the difference between an empty block and the same block when loaded, in many types of multisensors. It provided therefore a simple reading method, direct and parallel for all the multisensors.

In a preferred example, its implementation is described on a particular type of multisensors: the biochips. They comprise for example DNA chips, antibody chips, bacteria chips, virus chips, chromosome chips, protein chips, etc.

In the example of DNA chips, each block consists of a molecular layer with identical oligonucleotides capable hybridization with and only with their complementary strand. The DNA analysed is cut into strand of suitable length, amplified by the PCR technique, which means that each strand is replicated a great number of times, then turned into a solution in contact with the chip. The strands recognised are fixed by the corresponding wafers.

Our method enables to recognise the loaded wafers. In this view, the wafers whereof the thickness is regular and known, are taken as elements of the multilayer edifice, so that the assembly composed of base+multilayer+wafer or block constitutes a very high sensitivity optimised substrate. Under these conditions, the presence of additional strands after hybridization is detected easily by intensity or colour loading implied in the observation of the wafer by our display method. The quantity of material present on a wafer may also be assessed quantitatively by our measurement method.

The invention claimed is:

1. A device for ellipsometric two-dimensional display of a sample, comprising an object, placed in an incident medium, observed between a convergent light cross-reflected analyser and polarizer, wherein the ellipsometric parameters of the set composed of the object and a substrate whereon it is placed, are processed, characterised in that:
   the substrate comprises a base and a stack of layers and that its ellipsometric properties are known,
   the ellipsometric properties of the substrate being such that the variations of the ellipsometric parameters of the sample due to the object are displayed with a contrast greater than the contrast produced in the absence of such substrate.

2. A device for two-dimensional display of a sample according to claim 1, characterised in that the sample is irradiated through a wide-aperture lens such as a microscope lens.

3. A device for two-dimensional display of a sample according to claim 2, characterised in that the microscope is a microscope with differential interferential contrast.

4. A device for two-dimensional display of a sample according to claim 2, characterised in that the microscope is a fluorescence microscope.

5. A device for two-dimensional display of a sample according to claim 1, characterised in that the thickness e of the stack layer in contact with the object is such that the complex reflection coefficients $r_p$ and $r_s$ of the substrate verify the condition $d^2/de^2[Ln|r_{p+}r_s|]=0$.

6. A device for two-dimensional display of a sample according to claim 5, characterised in that the optical properties of the substrate are such that the minimum value taken by the quantity $|r_p+r_s|$ over the set of values of e is as small as possible.

7. A device for two-dimensional display of a sample according to claim 1, characterised in that it contains a polychromatic light source.

8. A device for two-dimensional display of a sample according to claim 1, characterised in that it contains a monochromatic light source.

9. A device for two-dimensional display of a sample according to claim 1, characterised in that the base is in silicon.

10. A device for two-dimensional display of a sample according to claim 1, characterised in that the stack consists of a single layer.

11. A device for two-dimensional display of a sample according to claim 10, characterised in that the layer is a silica layer.

12. A device for two-dimensional display of a sample according to claim 10, characterised in that the thickness of the silica layer is of the order of 1 025 Å, the incident medium being simply air.

13. A device for two-dimensional display of a sample according to claim 10, characterised in that the layer is a magnesium fluoride layer.

14. A device for two-dimensional display of a sample according to claim 10, characterised in that the layer is a polymer layer.

15. A device for two-dimensional display of a sample according to claim 10, characterised in that the layer is a polymer layer, with an optical index substantially equal to 1.343, the incident medium being simply air.

16. A device for two-dimensional display of a sample according to claim 10, characterised in that the layer is a mineral layer, with an optical index substantially equal to 1.74, the incident medium being simply water.

17. A device for two-dimensional display of a sample according to claim 10, characterised in that the layer is a mineral layer, with an optical index substantially equal to 1.945, the incident medium being an oil with an optical index of 1.5.

18. A device for two-dimensional display of a sample according to claim 10, characterised in that the layer is discontinuous and composed of silica blocks and with an index of 1.343, of the same height delineating the thickness of the layer and with cross-sectional dimensions significantly smaller than a micrometer, the incident medium being simply air.

19. A device for two-dimensional display of a sample according to claim 10, characterised in that the layer is a mesoporous or nanoporous mineral or organic layer with an index substantially equal to 1.343, the incident medium being simply air.

20. A device for two-dimensional display of a sample according to claim 10, characterised in that the layer is a mineral aerogel with an index substantially equal to 1.343, the incident medium being simply air.

21. A device for two-dimensional display of a sample according to claim 2, characterised in that it contains a microscope comprising an aperture diaphragm in the form of a longitudinal slot adjustable around the axis of the microscope enabling to restrict the illuminating cone to a single incidence plane in a selected direction.

22. A device for two-dimensional display of a sample according to claim 1, characterised in that it contains a microscope comprising an aperture diaphragm in the form of a ring limiting the illuminating cone of the sample around an angle of incidence.

23. A device for two-dimensional display of a sample according to claim 1, characterised in that the object is a thin film and the stack comprises a bevelled layer whereof the thickness varies in a monotonic fashion in a direction X along the surface.

24. A measuring method using the device of claim 23, characterised in that:
- the display device is cut parallel to the direction X into two elements,
- the thin film is deposited on one of said elements,
- both elements are deposited between a cross-reflected polarizer and analyser under a polarising microscope illuminated by polychromatic light, in order to form coloured interference fringes on each of the elements,
- the offset of the fringes formed respectively in each of the elements is measured in order to deduce therefrom the properties of the layer deposited on one of them.

25. A device for two-dimensional display of a sample according to claim 1, characterised in that the substrate is the bottom of a Petri box.

26. A device for two-dimensional display of a sample according to claim 1, characterised in that the sample is a matrix multisensor.

27. A device for parallel reading of a matrix multisensor according to claim 26, characterised in that each block or wafer of the matrix constitutes the last layer of the stack.

28. A device for parallel reading of a matrix multisensor according to claim 26, characterised in that the multisensor is a bacteria, virus, antigen, antibody, protein, DNA, RNA, chromosome chip.

* * * * *